(12) United States Patent
Schippers

(10) Patent No.: US 11,110,299 B2
(45) Date of Patent: Sep. 7, 2021

(54) PROTON-ARC BEAM DELIVERY SYSTEM

(71) Applicant: PAUL SCHERRER INSTITUT, Villigen PSI (CH)

(72) Inventor: Jacobus Maarten Schippers, Remigen (CH)

(73) Assignee: Paul Scherrer Institut, Villigen PSI (CH)

( * ) Notice: Subject to any disclaimer, the term of this patent is extended or adjusted under 35 U.S.C. 154(b) by 0 days.

(21) Appl. No.: 16/968,661

(22) PCT Filed: Jan. 17, 2019

(86) PCT No.: PCT/EP2019/051163
§ 371 (c)(1),
(2) Date: Aug. 10, 2020

(87) PCT Pub. No.: WO2019/154605
PCT Pub. Date: Aug. 15, 2019

(65) Prior Publication Data
US 2021/0001150 A1 Jan. 7, 2021

(30) Foreign Application Priority Data
Feb. 9, 2018 (EP) .................................. 18156088

(51) Int. Cl.
*A61N 5/10* (2006.01)
(52) U.S. Cl.
CPC ......... *A61N 5/1043* (2013.01); *A61N 5/1045* (2013.01); *A61N 5/1048* (2013.01); *A61N 2005/1087* (2013.01)

(58) Field of Classification Search
CPC .................. A61N 5/10; A61N 5/1048; A61N 5/1077–1083; A61N 2005/1074; A61N 2005/1087
See application file for complete search history.

(56) References Cited

U.S. PATENT DOCUMENTS 6,814,694 B1 11/2004 Pedroni
10,446,364 B1* 10/2019 Mizushima ............ H05H 7/001
(Continued)

FOREIGN PATENT DOCUMENTS

| EP | 3305368 A1 | 4/2018 |
| WO | 0100276 A1 | 1/2001 |
| WO | 2017156419 A1 | 9/2017 |

*Primary Examiner* — Eliza W Osenbaugh-Stewart
(74) *Attorney, Agent, or Firm* — Laurence A. Greenberg; Werner H. Sterner; Ralph E. Locher

(57) ABSTRACT

A particle beam therapy system delivers a particle beam for particle radiation therapy to a target volume in a patient from different treatment angles. The particle beam enters an active static magnetic field region perpendicularly to a magnetic field. Magnets and/or coils generate a cylindrically shaped magnetic field system with magnetic fields oriented axially in the magnetic field system. The active magnetic field region has an outer radial guiding field region and an inner radial bending field region, with an arc scan magnet system at an outer edge, a first number of coils generating a static magnetic guiding field that is predominantly effective in the outer radial guiding field region, and a second number of coils predominantly effective in an inner radial bending field region. A treatment control system controls the magnets and/or coils to guide the particle beam according to a treatment plan for the target volume of the patient.

12 Claims, 5 Drawing Sheets

(56) References Cited

U.S. PATENT DOCUMENTS

2003/0141460 A1\* 7/2003 Kraft .................... A61N 5/1078
250/492.1
2014/0014851 A1 1/2014 Asaba \* cited by examiner Different azimuthal positions of a small aperture in axial direction a)   b)

PROTON-ARC BEAM DELIVERY SYSTEM

BACKGROUND OF THE INVENTION

Field of the Invention

The present invention relates to a particle beam therapy system comprising a configuration of magnetic fields to enable the delivery of a particle beam for particle radiation therapy to a target volume in a patient from a variety of different treatment angles.

In all external irradiation treatments beams of electrons, photons (X-rays), protons or other ions are used to deliver a radiation dose in a target volume (for example a tumor) within a patient. However, in such treatments it is unavoidable that some radiation dose is also deposited in (healthy) tissue outside the target volume, even though this problem is less serious when using proton beams or ion beams instead of photon or electron beams. Therefore, various techniques are being used to further minimize the dose to healthy tissue.

In the mostly used "cross fire" technique, the beam is directed from several directions to the target volume in order to obtain a high dose in the target volume and a low dose in the surrounding tissue. If many angular directions are used, this technique dilutes the dose outside the target volume over a large volume, thereby causing a significant reduction of the local dose in healthy tissue outside the target volume, but achieving a high dose in the target volume at the same time.

In this technique the treatment angle (the direction from which the beam is reaching the patient) is set by rotating the beam delivery device (gantry) around the patient sequentially to the appropriate angular orientations. The center of the rotation, the so-called isocenter, is crossed by the beams from all directions used. The more different treatment angles are used, the more volume is irradiated over which the non-target dose is diluted. In this way the dose in tissue surrounding the target volume is minimized quite effectively. This dose dilution over non-target tissue can be optimized by applying a continuous (and rather large) range of treatment angles. This continuous range of angles is called an Arc. At the moment this so called Arc Therapy is one of the most common methods in irradiation therapy for photon beams. For example the RapidArc/TrueBeam systems of Varian, the VMAT approach of Elekta or the so called Tomo- or TomoHelical Spiral-therapy system of Accuray, all use a form of arc-irradiation for photon based radiotherapy.

An arc can consist of a continuous filling of an angular range, but it can also consist of the summation of many discrete angular directions at a small distance from each other. During the application of the arc, the beam intensity can be varied in the accelerator or in the beam transport system, and/or the speed by of changing the treatment angle can be varied. This intensity modulation within an arc can be applied for further improvement the dose distribution.

Also in particle beam therapy (which includes proton beam therapy) different beam directions are applied to optimize the dose distribution. In particle therapy the so-called "gantry" is the typically used beam delivery device that can rotate around the patient. This is a mechanical construction supporting the components (such as for example the magnets) of the final sections of a beam transport system in a proton therapy facility. A gantry typically used in proton therapy is a big (diameter 8-10 m) and heavy (100-200 tons) device. Together with a correct positioning of the patient table, rotation of the gantry enables an irradiation of the target from different directions, as for example disclosed in the U.S. Pat. Nos. 6,814,694 and 7,348,579.

However, due to its weight, size and various safety aspects the rotation speed of the gantry is limited to typically 360 degrees per minute. Therefore, proton or ion treatments are usually performed by applying only a few discrete treatment angles. Due to this mechanical limitation, arc therapy with a particle therapy gantry is difficult to perform and will take a relatively long time of a few minutes. However, several recently performed calculations of dose distributions show possible improvements in proton dose distributions obtained with proton arc-therapy.

SUMMARY OF THE INVENTION

It is therefore the objective of the present invention to provide a system for particle therapy that extends the technical possibilities of particle therapy, such as proton therapy, into the direction of the arc-therapy known for photons.

This objective is achieved according to the present invention by a particle beam therapy system comprising a configuration of magnetic fields, i.e. made by several groups of coils and, as an option, an iron enclosure consisting of a system of iron poles, surrounded by an iron yoke, for accurate shaping of the magnetic fields. This is to enable the delivery of a particle beam for particle radiation therapy to a target volume in a patient from a variety of different treatment angles, said system comprising:

a) a particle beam directed towards an active static magnetic field region wherein the direction of the incoming particle beam is substantially perpendicular to the direction of the static magnetic field in the active magnetic field region;

b) said active static magnetic field region comprising a plurality of magnets or coils being disposed to generate a cylindrically shaped magnetic field system filled with magnetic fields being oriented substantially in the axial direction of the cylindrically shaped magnetic field system, said magnetic field system comprising an outer guiding field region and an inner bending field region;

c) the plurality of magnets or coils are distinguished into:

c1) an arc scan magnet system being located at an outer edge of the cylindrically shaped magnetic field system; said arc scan magnet system effecting a small radial displacement and/or deflection of the particle beam, preferably within a very short time, for example in the order of a millisecond;

c2) a first number of coils generating a static magnetic guiding field for the incoming particle beam that has been initially deflected by the arc scan magnet system, said static magnetic guiding field being predominantly effective in the outer radial guiding field region of the cylindrically shaped magnetic field system and enclosing the inner radial bending field region; preferably this static magnetic field is shaped by means of a proper coil geometry and electric currents and optionally by an iron enclosure consisting of poles surrounded by a yoke;

c3) a second number of coils generating a static magnetic bending field for the particle beam leaving the magnetic guiding field, said static magnetic bending field being predominantly effective in the inner radial bending field region of the cylindrically shaped magnetic field system; preferably this static magnetic field is shaped by means of a proper coil geometry and electric currents and optionally by an iron enclosure consisting of poles surrounded by a yoke;

d) a central region encompassing a treatment table for the patient, said central region being surrounded by the inner radial bending field region of the cylindrically shaped magnetic field system;

e) components for particle beam dosimetry and/or particle beam monitoring and/or range compensation and/or pencil beam scanning, said components being disposed in or near the central region, preferably in a nozzle system being moveable relative to the treatment table; and f) a treatment control system to control the plurality of magnets and/or coils in order to bring the particle beam into the desired treatment angles according to a treatment plan determining dose information to be deposited by the particle beam in the target volume of the patient.

This concept offers the possibility to irradiate the target volume from a continuous or discontinuous range of treatment angles, to perform the so-called Arc-therapy as explained in the introductory part, in analogy to the Arc-therapy method used in photon-therapy. It is the outstanding advantage of this system that the beam delivery system does not need to be moved as this is inherent to nowadays particle beam gantry systems. With this system, the application of an arc (the delivery of the irradiation at different treatment angles) can be performed within the relatively short time span of approximately several seconds.

In a preferred embodiment of the present invention a collimator ring can be disposed to surround the central region. The collimator or range shifter ring enables the treatment control system to sharpen the particle beam to obtain better focusing at the target volume.

In a preferred embodiment of the present invention a range-shifter ring can be disposed to surround the central region. The range shifter ring enables the treatment control system to better focus the penetration depth of the particle beam to the target volume.

In order realize a pencil beam scanning treatment plan, a number of separate pencil beam scanning magnets is provided in between the outer radial region and the inner radial region or partially overlapping the inner radial region to generate a separately adjustable magnetic pencil beam scanning field.

In a further preferred embodiment of the present invention, a pulsed particle beam can be provided, for example a beam from a synchrocyclotron. When a pulsed beam is provided, the treatment angle can be changed in the time between the pulses. Thus, it has to be mentioned that the field strength of the guiding and the bending fields can be adjusted but this adjustments need to be completed when the next pulse of the particle beam is provided.

Typically for particle beam therapy, the particle beam can be a proton beam or an ion beam, such as a carbon ion beam or a helium ion beam.

For being enabled to deliver a precise dose deposition in the target volume at a variety of treatment angles, the treatment control system can realize the determined variety of treatment angles by an appropriate change of the magnetic strength caused by the arc scan magnet. Therefore, only the strength of the arc scan magnet system has to be changed causing the particle beam to go through the cylindrical magnetic guiding field at a slightly different position which results in a small change of the treatment angle at the target volume.

Preferred embodiments of the present invention are hereinafter described in more detail with reference to the attached drawings:

DETAILED DESCRIPTION OF THE INVENTION

Figure 1:
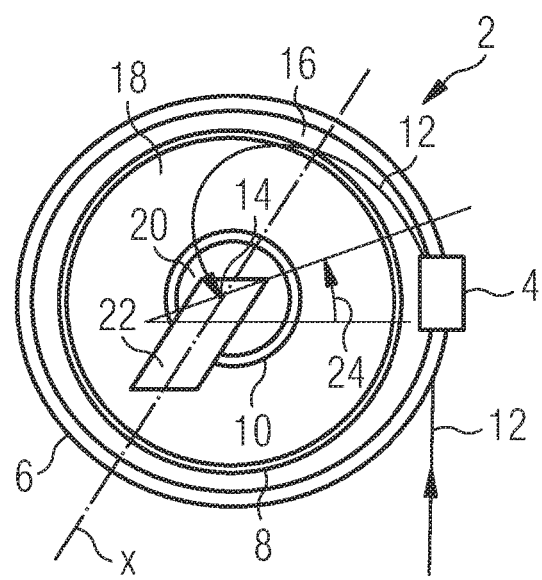
FIG. 1 schematically a front view of a layout of the particle beam therapy system.

The invention presented here deals with a concept of a configuration of concentric static magnetic fields with a fixed orientation and position in space, to deliver a proton beam to the target volume, i.e. a tumor volume in a patient, for radiation therapy from many different angles without mechanical movement of a beam delivery system around the patient. This concept enables the possibility to irradiate from a continuous range of angular directions at the patient position; in analogy to the method called Arc therapy which is frequently used in photon therapy. The concept that is presented here for proton beams is also applicable for any form of particle therapy with any other ion beam, such as those of carbon or helium.

The present invention (see FIGS. 1 and 2) comprises a system for particle beam therapy, here a proton beam therapy system 2. This proton beam therapy system 2 comprises a number of magnets 4 and coils 6, 8, 10 and optionally an iron enclosure that are fixed in space and that are used to deliver the proton beam 12 at the isocenter 14 of the system 2 from different directions (treatment angles 26, see FIG. 3). It is specific to this therapy system 2 that the treatment angle 26 at the isocenter 14 can be changed without moving any big magnet like this has to be effected in nowadays gantry systems (i.e. proton beam installations Gantry 1 and Gantry 2 at Paul Scherrer Institut, Villigen, Switzerland).

Figure 10:
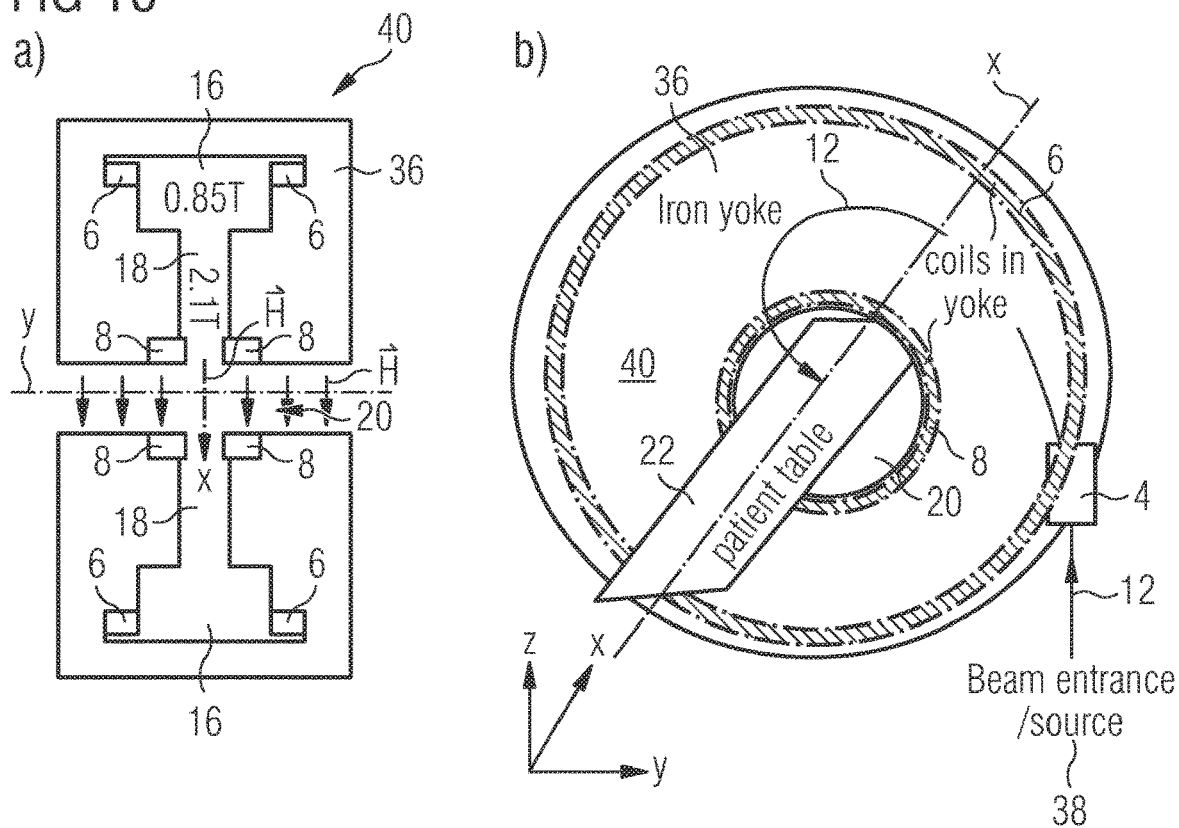
FIG. 10 schematically a cross-sectional side view (a) of a possible magnet arrangement of the iron enclosure, comprising an iron yoke surrounding iron poles and concentric coils for the generation of the static guiding and bending field and (b) a front view on this magnet arrangement.

The proton beam therapy system 2 is designed as a cylindrical system, comprising a system of magnets 4 and coils 6, 8, 10 generating at least an outer guiding field region 16 (static 0.8 T) and an inner bending field region 18 (static 2.1 T), both having concentric magnetic fields. The coils 6, 8, 10 are realizable as superconducting coils. The coils 6, 8, 10 can be optionally embedded in an iron enclosure, comprising a yoke and poles, as shown in FIG. 10. In general, the arrangement of the coils 6, 8, 10 and the iron has a similarity with the magnet configuration in a cyclotron. Thereby, the system of coils 6, 8, 10 and optional iron enclosure can benefit for example from the cyclotron principle where the magnetic field vectors are substantially parallel between the two pole shoes wherein the pole shoes are kept within a closed magnetic yoke. These concentric magnetic fields are surrounding a central region 20 which is a free cylindrical space around the axis x of the therapy system 2. The coils 6, 8, 10 are oriented perpendicular to this axis x and lay substantially parallel to the y-z plane. In the central region 20, a patient can be located on a treatment table 22. After the calculation of the therapy plan, the patient has to be positioned according to this plan in order to locate the target volume (for example a tumor in the patient) at the axis of the cylindrical system, which is the isocenter 14 of the irradiation treatment.

The concentric magnetic fields in both concentric regions 16, 18 are oriented in the same direction and approximately parallel to the cylinder axis (axis x). The magnetic field in an outer ring shaped guiding field region 16 is called here the "guiding field" and it surrounds an inner ring shaped bending field region 18 which is here called the cylindrical "bending field" region. The central region 20 is centered in this bending field region 18 and in addition to the coil 10 further coils or iron blocks can be added to the proton beam therapy system 2 to minimize the magnetic field strength in the central region 20.

The particle beam 12 from an accelerator (for example a cyclotron) is entering the guiding field region 16 in tangential direction through the arc-scan magnet system 4, located at the outer edge of the guiding field region 16. The arc-scan magnet system 4 can comprise two dipole magnets which direct the proton beam 12 into an almost circular orbit within the ring of the guiding field region 16. The beam trajectory is not exactly centered in the ring and will gradually approach the inner edge of the guiding field region 16. This location is controlled by the direction the proton beam 12 initially had when the proton beam 12 has left the arc-scan magnet system 4. This direction is controlled by the strength of the magnetic field of the arc-scan magnet system 4.

Thus, after a certain azimuthal angle has been covered by the proton beam 12 in the guiding field region 16, the proton beam 12 will reach the inner edge of the guiding ring and will enter the bending field region 18. This bending field is stronger than the guiding field thereby being enabled to bend the proton beam 12 to the axis (the isocenter 14) of the proton beam therapy system 2.

Figure 3:
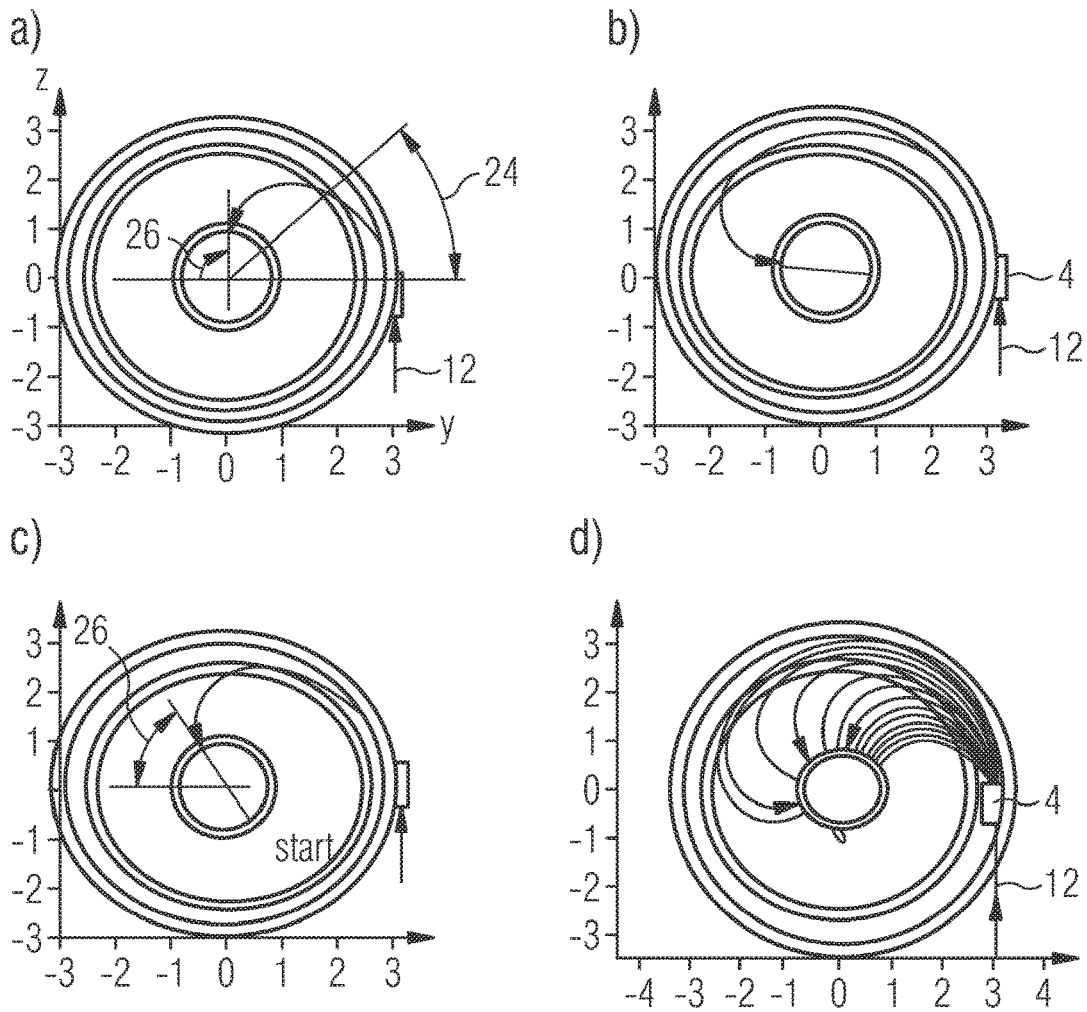
FIG. 3 schematically a number of front views of possible layouts of the particle beam therapy system.

As shown schematically in FIG. 3, the setting of the small arc-scan magnet system 4 is determining at which azimuthal angle 24 the proton beam 12 will enter the inner ring shaped bending field region 18 with the stronger bending field. As shown in FIG. 3, the proton beam 12 will reach the isocenter 14 along a radial direction determining the treatment angle 26. Thus, following these proton beam controls stemming from a treatment control system (not shown in detail), the setting of the arc-scan magnet system 4 will determine at which treatment angle 26 the beam will reach the patient. By using a constant ratio between the guiding field and the bending field and an energy dependent absolute magnitude of these fields, the only setting to be made is the setting of the strength of the arc-scan magnet system 4 to the desired field strength in order to set the treatment angle 26 at the patient. Since a change of the strong magnetic guiding field and the bending field would need much more effort, power and time, the arc-scan magnet system 4 is designed such, that it can apply very fast changes of the treatment angle 26 at the patient. Consequently, an arc (a variety of proton beam deliveries at different treatment angles 26) of a considerable dimension (therapy relevant arc), such as shown in the FIG. 3d, can be covered in only a few seconds.

The azimuthal arc can be covered in a continuous sweep or in many small discrete steps, or in a combination of these methods, as shown in FIG. 3d and FIG. 4a (comprising an arc scan magnet system with two arc scan magnets 4a and 4b). If the proper isochronicity between the beam pulse, the beam characteristics and the treatment angle 26 can be achieved, this system can also be applied with a pulsed particle beam 12, for example with the beam stemming from a synchrocyclotron. At each step or pulse (sequence) the arc-scan magnet system 4 must then be kept constant at the appropriate field strength belonging to the respective discrete azimuthal angle 24. FIG. 4b schematically illustrates a front view of a possible layout of the invention showing a situation in which a scan over approximately 360 degrees is performed by using an arc scan magnet system 4 comprising two small magnets 4, 4c, which enable to change the position of the particle beam 12 in the guiding field region 16.

Figure 6:
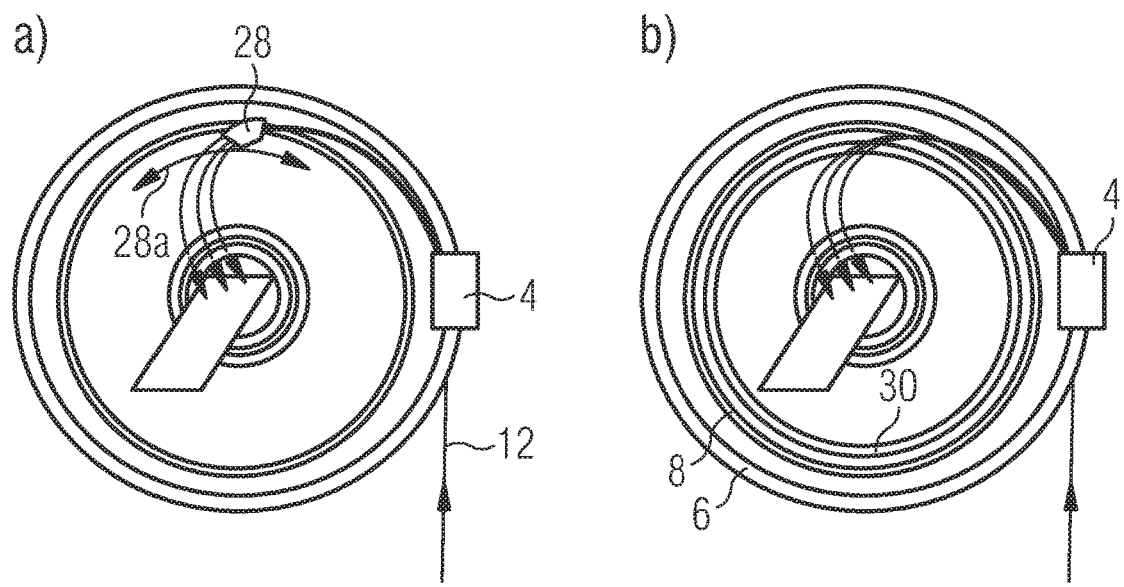
FIG. 6 schematically two ways to implement Pencil Beam Scanning in the particle beam therapy system.

In case the pencil beam scanning technique is to be applied in this system, lateral scanning is performed either by a small local or global adjustment coil 30 of the bending field, or by a separate pencil-beam scanning magnet (PBS-magnet 28) moving with the proton beam along an arrow 28a around the patient. Both possibilities are schematically shown in FIG. 6 (separate movable PBS magnet 28 in FIG. 6a and additional adjustment coil 30 in FIG. 6b).

The present invention achieves the objective of a therapy system 2 for the treatment of cancer with proton or other ion beams, in which a magnetic field configuration can apply a wide range of incident beam directions (treatment angles 26) at the patient without the need of any mechanical motion of the magnetic system and with the possibility to change the treatment angle 26 much faster than with currently used gantries.

This objective is achieved according to the present invention by the system of magnets that are fixed in space and which guides the proton or ion beam to the isocenter 14. The therapy system 2 examplarily comprises a cylindrical system generating at least the two regions 16, 18 of concentric magnetic fields, surrounding a free space (central region 20) in which the patient to be treated can be located on a treatment table 22.

Figure 2:
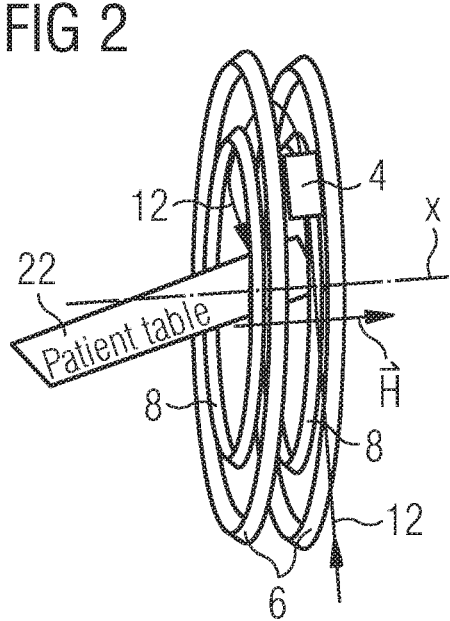
FIG. 2 schematically a side view of a layout of the particle beam therapy system according to FIG. 1.
Figure 4:
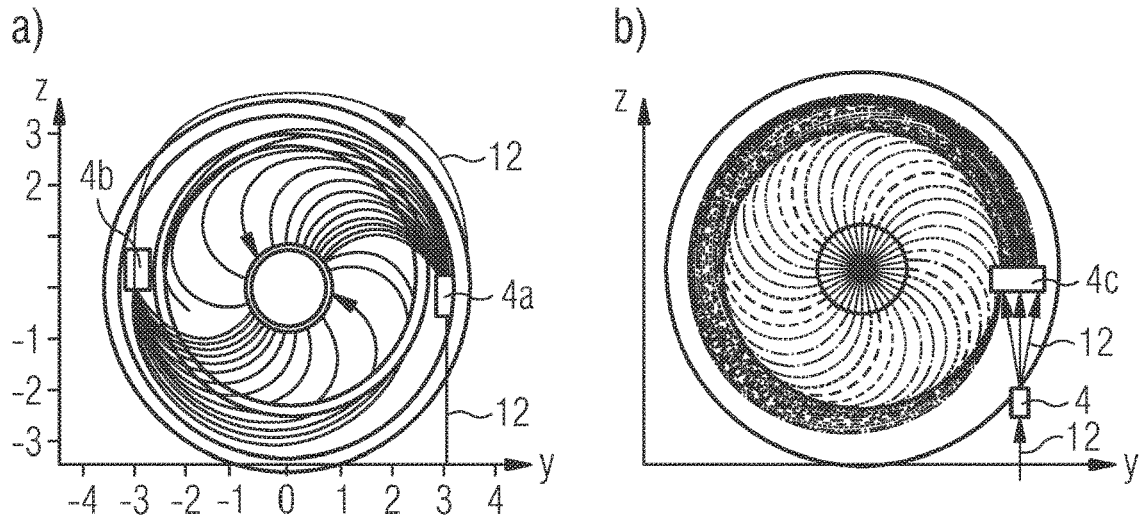
FIG. 4 schematically in part a) a front view of a possible layout of the invention showing a situation in which a scan over approximately 360 degrees is performed by using two separate arc scan magnet systems and schematically in part b) a front view of possible layout of the invention showing a situation in which a scan over approximately 360 degrees is performed by using a single arc scan magnet system consisting of two small magnets, which enable to change the position of the particle beam in the guiding field.
Figure 5:
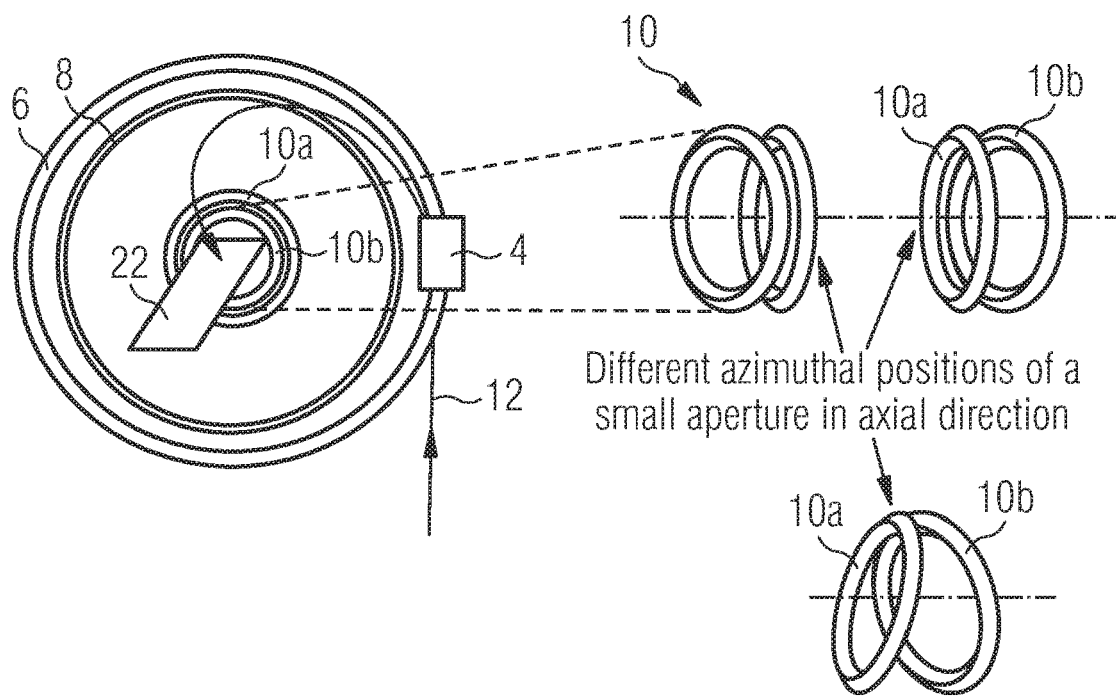
FIG. 5 schematically a collimation and/or range shifter system that is mounted in or around the patient in the central region of the particle beam therapy system.
Figure 7:
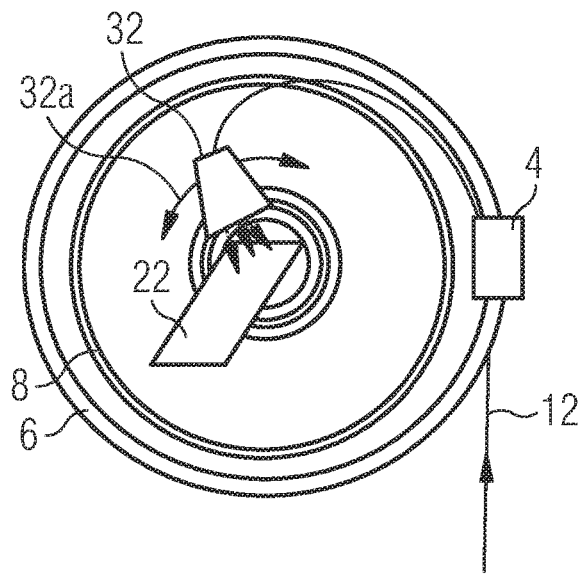
FIG. 7 schematically the implementation of a nozzle system.
Figure 8:
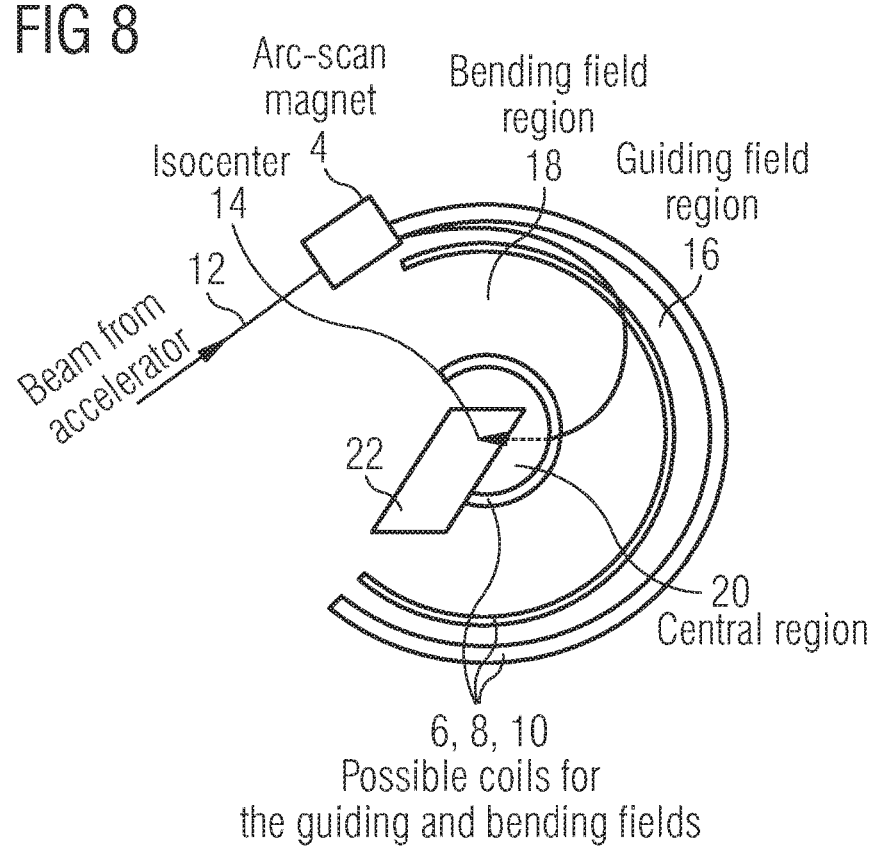
FIG. 8 schematically a front view of a layout of the particle beam therapy system having the option of partial coverage of the cylinder with an aperture to access the patient from the side.
Figure 9:
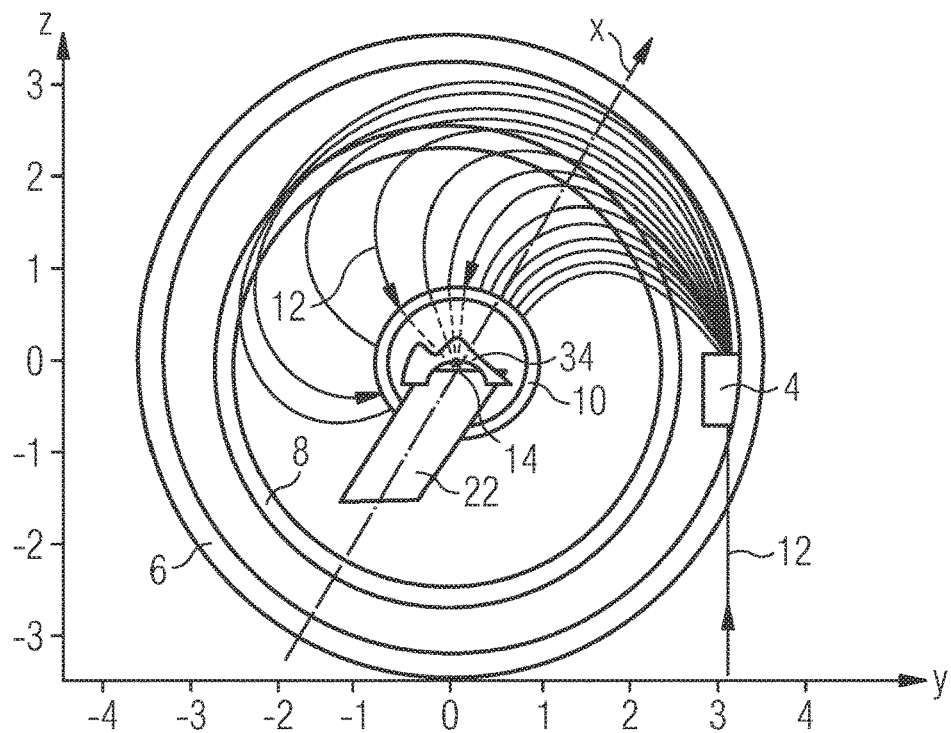
FIG. 9 schematically a front view of a layout of the particle beam therapy system comprising a range compensator covering the patient and shifting the range of the incoming beam as a function of treatment angle.

Optionally, range compensation material 34, mounted close to the patient or mounted on two mechanical rings in the central region, to obtain a correct range of the particle beam 12 in the patient for all treatment angles 26 thereby enabling a reduction of the number of required beam energies per treatment (see FIG. 9);

The present invention also includes one or more of the following options of different embodiments of the system:

a) at least two arc-scan magnets 4a, 4b are implemented in the therapy system 2 to reduce the length of the orbit in the guiding field; the external beam transport system is enabled to sequentially send the beam 12 to the arc scan magnets 4a, 4b. A schematic view of a possible layout of this option is shown in FIG. 4;

b) the treatment angle 26 can be set by the arc scan magnet system 4 together with an additional small change of the bending field and/or the guiding field;

c) the magnets generating the static guiding field and the static bending field can be constructed by a magnet system based on two parallel sets of at least two concentric coils 6, 8, 10, see FIGS. 1 and 2, optionally in combination with an iron enclosure consisting of a yoke surrounding a system of iron poles, see FIG. 10;

d) the magnets generating the guiding field and the bending field can be constructed by a magnet based on several sets of concentrically mounted "race track-type" coil systems;

e) two parallel rings 10a, 10b mounted in the central region 20 around the patient serve as a beam collimator 10 limiting the beam spread in the axial direction (see FIG. 5);

f) two parallel rings 10c, 10d mounted in the central region 20 around the patient serve as a range shifter adjusting the beam range in the beam direction (see FIG. 5); f) the therapy system 2 is equipped with a range compensator 34 in the central region 20 between the patient and the incoming beam 12 in order to adjust the range of the incoming beam as a function of treatment angle 26, see FIG. 9;

g) the therapy system 2 is equipped with a collimation system 10 to limit the beam size at the patient;

h) by using an appropriate patient table 22 and a respective treatment control system, the therapy system 2 is made suitable for the application of spiral-therapy; in this application, the patient is moving along the axis x of the therapy system 2 during the application of the arc doses (example of the dose delivery as arc of beam deliveries in FIG. 9);

i) for Pencil Beam Scanning (PBS), a small and fast PBS magnet 28 can be mounted in the inner ring shaped region 18 of the bending field, preferably at the outer side of bending field. This PBS magnet 28 is movable in order to set its azimuthal position according the respective azimuthal position of the proton beam 12, see FIG. 6a;

j) in the realization of another option for the Pencil Beam Scanning, the field in the bending region, or a separately controlled field as shown in FIG. 6b with the coil 30 in a inner ring shaped bending field region 18 at the outer radial edge of the bending field region 18, can be used to perform the PBS, see FIG. 6b;

k) the therapy system 2 is equipped with a nozzle system 32 located in the bending field region, in which the particle beam 12 is scanned or scattered, monitored and collimated; the nozzle system 32 is moveable along an arrow 32a and its azimuthal position must comply with the azimuthal position of the particle beam, see FIG. 7;

l) the therapy system is not encompassing the full 360 degree circumference of a cylinder, but only a segmental part of the cylindrical system; this segment shall cover at least 180 degrees of the full cylinder; this option increases the access possibilities to the central region 20 and will enable more patient table orientations; FIG. 8 shows a possible layout of such an open therapy system;

m) a further option could be to minimize or the magnetic field in the central region 20; and n) a specially shaped magnetic field and an MRI-specific equipment can be added to the central region; by additionally adding appropriate magnetic shielding or compensation between this region and the surrounding magnetic fields, this option also enables the acquisition of MRI-images during, immediately before or immediately after the irradiation with particle beams.

In detail, FIG. 1 shows a schematic front view of a proton beam therapy system 2 in which the major components are indicated.

FIG. 2 illustrates a schematic side view of the layout according to FIG. 1, also showing the major components of the proton beam therapy system 2.

FIG. 3 schematically depicts a number of front views of possible layouts of the therapy system 2. In particular, several different azimuthal angles 24 and treatment angles 26 are shown at the patient, as set by the arc scan magnet 4. The lower right FIG. 3d) shows the situation in which one arc-scan magnet sweeps over the upper 180 degrees of treatment angles 26. The optimal location of the arc scan magnet 4 along the outer edge of the guiding field depends on the direction and location of the incoming particle beam from the accelerator and the beam transport system upstream of the therapy system 2. The location of the arc scan magnet 4, 4a, 4b in these figures represents just possible examples.

FIG. 4a) schematically illustrates a front view of two possible layouts of the therapy system 2. FIG. 4a) is representing a situation where a scan can be performed over a range of approximately 360 degrees by using two arc-scan magnets 4a, 4b. The particle beam 12 can be sent from a first arc scan magnet 4a to a second arc scan magnet 4b using a respective extension of the guiding field. In this example for the therapy system 2 a sweep is performed with the first arc scan magnet 4a to covering the upper 180 degrees and a sweep is performed with the second arc scan magnet 4b to cover the lower 180 degrees of the treatment angles 26. This example particularly shows the options that are present by using a second or multiple arc-scan magnet systems. FIG. 4b schematically illustrates a front view of a possible layout of the invention showing a situation in which a scan over approximately 360 degrees is performed by using an arc scan magnet system comprising two small dipole magnets 4, 4c, which enable to change the position of the particle beam in the guiding field.

FIG. 5 schematically shows an embodiment of the particle therapy system 2 that comprises a collimation or range shifter system 10. This collimation or range shifter system 10 is mounted around the patient table 22 in the central region 20. The collimation and the range shifter system each comprise two parallel rings 10a, 10b. The shape of each ring of the range shifter is wedge shaped. The aperture of the collimator in the axial direction or the overlap of the two range-shifter rings, is set by adjusting the tilting of the two rings 10a, 10b, so that the axial distance between the rings is set to the correct axial aperture or overlap at this angle. At the right hand side of the FIG. 5, three possible azimuthal locations (left, right and top) of the aperture are shown.

FIG. 6 schematically illustrates two possible ways to implement the Pencil Beam Scanning in the particle beam system. In the left FIG. 6(a) a PBS-magnet 28 is mounted at the outer edge of the bending field region. By controlling the PBS magnet 28 properly, the PBS magnet 28 scans the particle beam 12 in the transversal direction(s). The PBS-magnet 28 is moveable in order rotate over an arc around the system axis x to be aligned with the respective azimuthal beam position. Three different scanned beams are indicated schematically. In the right FIG. 6(b) the PBS is performed by adjusting the field in the inner ring with an PBS ring coil 30 within the bending field region 18. The figure shows an example of a PBS-field configuration in which the PBS ring coil 30 has been mounted at the external edge of the bending field. Three different scanned beams are indicated schematically, too.

FIG. 7 schematically represents an embodiment of the particle therapy system implementing a nozzle system 32. This nozzle system 32 can comprise equipment that performs beam monitoring, beam collimation, and scattering or pencil beam scanning. The nozzle system 32 is moveable in order to rotate along an arc around the system axis x to be aligned with the respective azimuthal beam position.

FIG. 8 schematically depicts a front view of a possible layout of the particle beam system taking into account a specific need to access the patient table 22. With the option of only a partial coverage of the cylinder by the concentric magnetic fields, an aperture enables an access to the patient from one side. The option with the magnetic system on the right side is shown. This could also be at the left side or at the top side.

FIG. 9 schematically addresses the option of providing additional means for compensating the range of the particle beam. This range compensator 34 can be designed as a cushion that is shown in the front view here. The range compensator 34 covers the patient at least in the area of treatment and shifts the range of the incoming beam 12 as a function of the treatment angle 26 and the depth of the range compensator 34.

FIG. 10 schematically illustrated an example for the design of the plurality of magnets 4, 6, 8. FIG. 10*a*) shows the orientation of the coils 6, 8 which generate the guiding field in the outer ring shape region 16 and the bending field in the inner ring shaped region 18. The coils 6, 8 producing a magnetic field H are embedded in an iron enclosure, consisting of a yoke 36 and a system of magnet poles, which define the exact shape of the static magnetic field in the system. FIG. 10*b*) shows a top view on this arrangement. The arrangement in this example has the same configuration as the magnet of a cyclotron where a strong cylindrical magnetic field causes a charged particle beam to travel along a ring-shaped trajectory. Since here no HF electric field is present, the particles in the beam 12 entering the H-field at a direction perpendicular to the H-field do not gain energy from the HF-field and are therefore be bent to the isocenter 14.

The invention claimed is:

1. A particle beam therapy system with a configuration of magnetic fields for delivering a particle beam for particle radiation therapy to a target volume in a patient from different treatment angles, the system comprising: a) a particle beam directed towards an active static magnetic field region, a direction of the particle beam incoming into said magnetic field region being substantially perpendicular to a direction of a magnetic field in said magnetic field region; b) said active static magnetic field region having a plurality of magnets and/or coils disposed to generate a cylindrically shaped magnetic field system filled with magnetic fields that are oriented substantially in an axial direction of said cylindrically shaped magnetic field system, said magnetic field region including an outer radial guiding field region and an inner radial bending field region; c) said plurality of magnets and/or coils being distinguished into: c1) an arc scan magnet system located at an outer edge of said cylindrically shaped magnetic field system; said arc scan magnet system effecting a radial displacement and angle to the particle beam, determining a location where the particle beam enters the guiding field region; c2) a first number of coils, optionally embedded in an iron enclosure, for generating a static magnetic guiding field for the incoming particle beam that has been initially deflected by said arc scan magnet system, the magnetic guiding field being predominantly effective in said outer radial guiding field region of said cylindrically shaped magnetic field system and enclosing said inner radial bending field region; c3) a second number of coils, optionally embedded in an iron enclosure, for generating a static magnetic bending field for the particle beam exiting said magnetic guiding field region, the magnetic bending field being predominantly effective in said inner radial bending field region of said cylindrically shaped magnetic field system; d) a central region encompassing a treatment table for the patient, said central region being surrounded by said inner radial region of said cylindrically shaped magnetic field system; and e) a treatment control system configured to control said plurality of magnets and/or coils in order to bring the particle beam into the desired treatment angles according to a treatment plan determining dose information to be deposited by the particle beam in the target volume of the patient.

2. The system according to claim 1, further comprising a nozzle system movably disposed relative to the treatment table, said components being disposed in said nozzle system.

3. The system according to claim 1, wherein said first number of coils are embedded in an iron enclosure and said second number of coils are embedded in an iron enclosure.

4. The system according to claim 1, further comprising a set of collimator rings disposed to surround said central region.

5. The system according to claim 1, further comprising a set of range shifter rings disposed to surround said central region.

6. The system according to claim 1, further comprising a plurality of pencil beam scanning magnets in between said outer radial guiding field region and said inner radial bending field region, or partially overlapping said inner radial bending field region to generate a separately adjustable magnetic pencil beam scanning field.

7. The system according to claim 6, wherein the particle beam is a carbon ion beam or a helium ion beam.

8. The system according to claim 1, wherein the particle beam is a proton beam or an ion beam.

9. The system according to claim 1, wherein said treatment control system is configured to adjust the determined variety of treatment angles by an appropriate change of a magnetic strength generated by said arc scan magnet system.

10. The system of claim 1, further comprising a component selected from a group consisting of a component for particle beam dosimetry and a component for particle beam monitoring, said component being disposed in said central region.

11. The system of claim 1, further comprising a component for range compensation, said component being disposed in said central region.

12. The system of claim 1, further comprising a component for pencil beam scanning, said component being disposed in said central region.

* * * * *